(12) United States Patent
Osawa et al.

(10) Patent No.: US 11,497,415 B2
(45) Date of Patent: Nov. 15, 2022

(54) MASK SIZE GAUGE (71) Applicant: NIHON KOHDEN CORPORATION, Tokyo (JP)

(72) Inventors: Risa Osawa, Tokorozawa (JP); Raku Ishida, Tokorozawa (JP); Masayuki Suzukawa, Tokorozawa (JP); Yuya Baba, Tokorozawa (JP); Masayuki Inoue, Tokorozawa (JP); Isao Matsubara, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 329 days.

(21) Appl. No.: 16/874,888

(22) Filed: May 15, 2020

(65) Prior Publication Data

US 2020/0375498 A1   Dec. 3, 2020

(30) Foreign Application Priority Data

May 27, 2019  (JP) .............................. JP2019-098577

(51) Int. Cl.
*A61B 5/107* (2006.01)
*G01B 3/04* (2006.01)
*G01B 3/00* (2006.01)

(52) U.S. Cl.
CPC .......... *A61B 5/1072* (2013.01); *A61B 5/1075* (2013.01); *G01B 3/04* (2013.01); *G01B 3/004* (2013.01)

(58) Field of Classification Search
None
See application file for complete search history.

(56) References Cited

U.S. PATENT DOCUMENTS

| 4,173,074 | A  | * | 11/1979 | Newman | ............... | A41D 19/046 |
| | | | | | | 33/2 R |
| 5,584,125 | A  | * | 12/1996 | Prete | ...................... | A61M 16/06 |
| | | | | | | 33/501.45 |
| 7,603,787 | B1 | * | 10/2009 | Butler, III | ................. | B07C 1/10 |
| | | | | | | 33/501.45 |
| 8,176,647 | B2 | * | 5/2012 | Masley | ..................... | G01B 5/02 |
| | | | | | | 33/2 R |
| 8,307,560 | B2 | * | 11/2012 | Tulin | ................. | G06Q 30/0201 |
| | | | | | | 33/17 R |
| 10,314,996 | B2 | | 6/2019 | Tang Ee Ho et al. | | |
| 10,835,359 | B2 | * | 11/2020 | Wagner | ................... | A61B 3/111 |

(Continued)

FOREIGN PATENT DOCUMENTS

| JP | 2017-530740 A | 10/2017 | | |
| WO | WO-2013102824 A1 | * | 7/2013 | ........... A61B 5/1077 |
| WO | WO-2015084190 A1 | * | 6/2015 | ............. A61B 5/107 |

*Primary Examiner* — Christopher W Fulton
(74) *Attorney, Agent, or Firm* — Pearne & Gordon LLP (57) ABSTRACT

A mask size gauge for selecting a size of a mask in accordance with a distance in a height direction between an upper reference part in an upper portion of a face of a wearer, and a lower reference part in a lower portion, includes: a reference position indicating portion indicating that the reference position indicating portion is to be placed at a height position of the upper reference part on an outer lateral side of an eye of the wearer; and a size indicating portion that is located at a position which is closer to a middle of the face than the reference position indicating portion, and that indicates the size of the mask according to a height position of the lower reference part.

18 Claims, 5 Drawing Sheets

(56) References Cited

U.S. PATENT DOCUMENTS

| | | | |
|---|---|---|---|
| 10,968,642 B1* | 4/2021 | Rasmussen | G01B 5/0004 |
| 2011/0214305 A1* | 9/2011 | Nunes | A61B 5/1071 |
| | | | 33/512 |
| 2012/0323126 A1* | 12/2012 | Estocado | A61B 5/743 |
| | | | 600/587 |
| 2015/0007439 A1* | 1/2015 | Todd | G01B 3/38 |
| | | | 33/512 |
| 2015/0089824 A1* | 4/2015 | Moore | A41H 1/02 |
| | | | 33/512 |
| 2018/0008794 A1* | 1/2018 | Salmon | A61M 16/0622 |
| 2021/0145316 A1* | 5/2021 | Groman | A61B 5/1072 |

* cited by examiner

MASK SIZE GAUGE

CROSS-REFERENCE TO RELATED APPLICATIONS

This application is based upon and claims the benefit of priority from prior Japanese patent application No. 2019-098577, filed on May 27, 2019, the entire contents of which are incorporated herein by reference.

TECHNICAL FIELD

The presently disclosed subject matter relates to a mask size gauge that is used for selecting the size of an oxygen mask or a ventilator mask in accordance with a wearer.

BACKGROUND ART

A technique in which, in order to measure the size of a medical mask, a ruler is placed close to the front of the face of a wearer, and the size that is indicated on the ruler is read (for example, see JP-T-2017-530740).

However, the placement in which the ruler is placed close to the front of the face of the wearer may sometimes cause a feeling of discomfort in the wearer, and a medical person or the like tends to hesitate to perform such a measurement. Therefore, there is a possibility that a mask of an adequate size cannot be easily selected.

The invention has been conducted in view of the above-described problem. It is an object of the presently disclosed subject matter to enable a mask of an adequate size to be easily selected without causing a feeling of discomfort in a wearer.

SUMMARY OF INVENTION

According to an aspect of the presently disclosed subject matter, there is provided a mask size gauge for selecting a size of a mask in accordance with a distance in a height direction between an upper reference part in an upper portion of a face of a wearer, and a lower reference part in a lower portion, the mask size gauge comprising: a reference position indicating portion indicating that the reference position indicating portion is to be placed at a height position of the upper reference part on an outer lateral side of an eye of the wearer; and a size indicating portion that is located at a position which is closer to a middle of the face than the reference position indicating portion, and that indicates the size of the mask according to a height position of the lower reference part According to an aspect of the presently disclosed subject matter, there is also provided a mask size gauge for selecting a size of a mask in accordance with a distance in a height direction between an upper reference part in an upper portion of a face of a wearer, and a lower reference part in a lower portion, the mask size gauge comprising: a size indicating portion that indicates the size of the mask according to a height position of the upper reference part in an outer lateral side of an eye of the wearer; and a reference position indicating portion indicating that the reference position indicating portion is to be placed at a position which is closer to a middle of the face than the size indicating portion, and at a height position of the lower reference part.

DESCRIPTION OF EMBODIMENTS

Hereinafter, embodiments of the presently disclosed subject matter will be described with reference to the drawings. In the following description of each of the embodiments, a component that has the same or similar function as that in another embodiment is denoted by the identical reference numeral, and its description is omitted, or its illustration and description are omitted.

Embodiment 1

Figure 1:
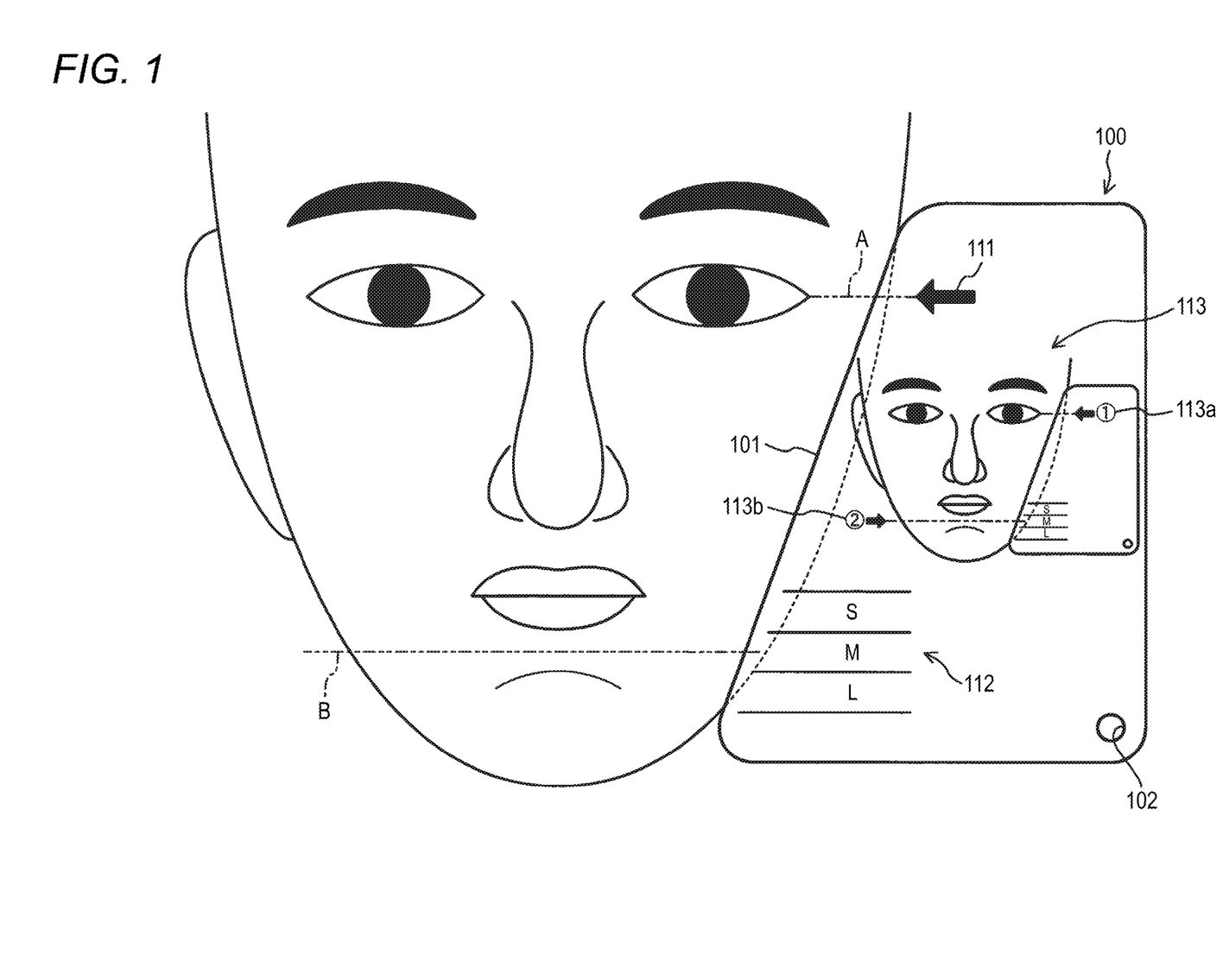
FIG. 1 is a front view illustrating an example of a mask size gauge of Embodiment 1.

A mask size gauge 100 of Embodiment 1 is formed by a resin plate or the like that has a trapezoidal shape as illustrated in, for example, FIG. 1. In a posture during use that is illustrated in the figure, more specifically, the mask size gauge 100 has a trapezoidal shape including an oblique side portion 101, a vertical side portion that is opposed to the oblique side portion 101, and horizontal side portions that are formed in the upper and lower edges, respectively. In the trapezoidal shape, each of the vertices may be rounded or chamfered.

A reference position indicating portion 111 where, for example, an arrow shape is printed is disposed in the vicinity of the upper portion of the oblique side portion 101 so as to indicate that, as indicated by a reference letter A in FIG. 1, the reference position indicating portion 111 is to be placed at the height position of the eye (upper reference part) of a wearer on the outer lateral side of the eye. A size indicating portion 112 where, for example, four horizontal index lines and letters S, M, and L are printed is disposed in the vicinity of the lower portion of the oblique side portion 101 so as to indicate the adequate mask size according to the height position of the mentolabial sulcus (lower reference part) indicated by, for example, a reference letter B in the figure.

Here, the size indicating portion 112 is located at a position that is closer to the middle of the face than the reference position indicating portion 111, and the oblique side portion 101 is formed so as to connect together the reference position indicating portion 111 and the size indicating portion 112. According to the configuration, while preventing the mask size gauge 100 from being located in the front of the face of the wearer to cover the face or the eyes, the reference position indicating portion 111 can be placed at the height position of the eye of the wearer on the outer lateral side of the eye, and the size indicating portion 112 can be placed close to the mentolabial sulcus of the wearer, thereby enabling the size of a mask to be easily known in accordance with the height position of the mentolabial sulcus.

Although not essential, in the mask size gauge 100, a hole 102 is formed in the vicinity of the lower end of the vertical side portion so that a strap can be attached to the mask size gauge 100, or the mask size gauge 100 can be hung on a hook.

In the mask size gauge 100, an instruction indicating portion 113 configured by an illustration that indicates the use state of the mask size gauge 100, and that includes a similar figure of the mask size gauge 100 in which the size is reduced is disposed in the vicinity of a region between the reference position indicating portion 111 and the size indicating portion 112, or more specifically in a portion that is, for example, slightly above the middle portion, and that is hardly hidden when the lower right portion of the mask size gauge 100 is held in the hand. The illustration includes sequence indications 113a, 113b of the measurement procedure sequence. From the illustration, the user can easily know the followings. That is, the user is requested only to, when the mask size gauge 100 is used, cause the reference position indicating portion 111 to coincide with the eye height position A, and then read the index line of the size indicating portion 112 to which the height position B of the mentolabial sulcus corresponds. FIG. 1 illustrates the example in which the mask size gauge 100 is placed on the right side facing the wearer, i.e., that in which the measurement is performed while the right end of the mask size gauge 100 is held by the right hand, and the the gauge is moved close to the face. Also the illustration of the instruction indicating portion 113 in the figure indicates an example corresponding to the above-described placement.

As described above, the size of a mask can be selected while placing the mask size gauge 100 on the lateral side of the face of the wearer, and therefore it is possible to easily avoid a situation where the face or eyes of the wearer are covered by the mask size gauge 100, and a feeling of discomfort is caused. In the case where the mask is to be replaced with a new mask of another kind in accordance with the therapeutic strategy, for example, the three-dimensional shape of the mask hardly disturbs an operation such as that in which the scale is put on the face of the wearer from the front side of the wearer. Therefore, the size of a mask can be easily correctly measured.

The mask size gauge 100 has the shape in which the portion that is to be located on the lower lateral side of the face is placed close to the middle of the face. In the face of the wearer, therefore, the area of the portion that is covered by the mask size gauge 100 can be reduced, and hence it is possible to avoid a situation where a feeling of discomfort is given to the subject. Moreover, the mask size gauge has the above-described shape. Even in the case where the subject has already worn a mask, therefore, the size of a mask can be correctly measured without giving a feeling of discomfort to the subject or wearer, and the unnecessity of attachment and detachment of the mask can improve the quality of the medical treatment. Also in the case where there arises a necessity for replacing an oxygen mask with a non-invasive positive pressure ventilation (NPPV) full-face mask in accordance with a condition change, when the above-described mask size gauge 100 is used, for example, an adequate NPPV full-face mask can be selected even in a state where the oxygen mask remains to be attached to the face, and therefore it is possible not only to avoid a feeling of discomfort of the subject, but also to improve the quality of the medical treatment.

Since the mask size gauge 100 is formed into a trapezoidal shape as described above, the vicinity of the lower end of the vertical side portion of the mask size gauge 100 can be easily gripped, the rigidity of the mask size gauge 100 can be ensured, and it is possible to easily confirm that there is no inclination of the mask size gauge 100, by using the vertical side portion and the upper and lower horizontal side portions.

Although, in the above description, the embodiment in which the size of a mask is selected in accordance with the height position B of the mentolabial sulcus has been described, the manner of the selection is not limited to this, and the size may be selected in accordance with the height position of one of the lower end of the chin, the front end of the chin, the superior lip, the inferior lip, the boundary between the superior and inferior lips, the phitrum, and the like.

Although, in the above description, the embodiment in which the reference position indicating portion 111 is placed at the height position A has been described, the placement position is not limited to this. The portion may be placed at a height position of one of the eye inner corner, the eye outer corner, the center of the pupil in a front view, the eyebrow, and the like.

Although the instruction indicating portion 113 is indicated by the illustration so that the use method is understood easily and intuitively, the manner of instructing the use method is not limited to this, and the measurement procedure may be described by words, or the like.

Although the position of the instruction indicating portion 113 is not particularly limited, it is usually preferable that the portion is disposed at a position where, even when the mask size gauge 100 is held by the hand during the measurement, the portion can be viewed.

Alternatively, the mask size gauge 100 may be formed by an opaque material, and the reference position indicating portion 111 and the like may be disposed on the both surfaces so that, even when the mask size gauge 100 can be placed on either side of the face of the wearer, or, that is, the mask size gauge 100 is held by either or right or left hand, the measurement can be easily conducted.

Embodiment 2

Figure 2:
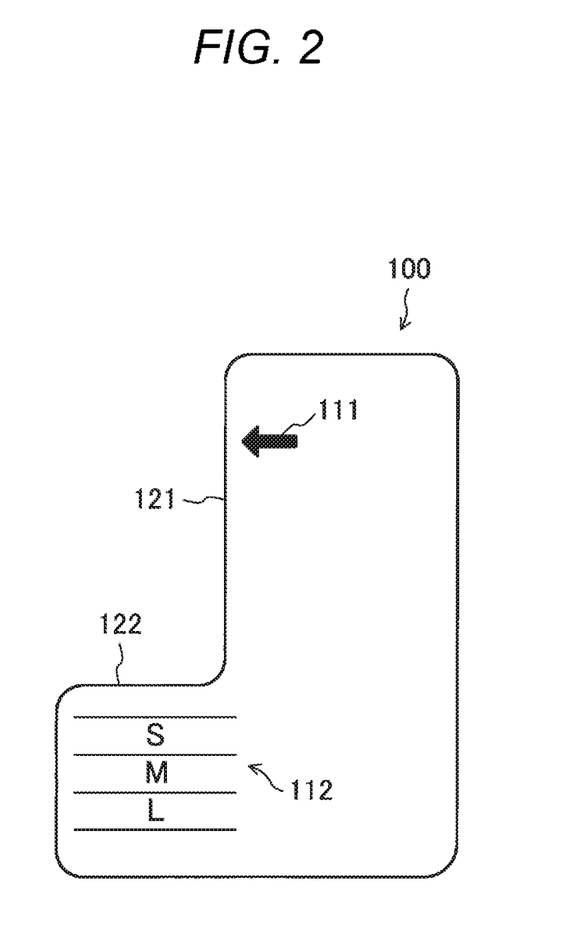
FIG. 2 is a front view illustrating an example of a mask size gauge of Embodiment 2.

The mask size gauge 100 of Embodiment 2 may be formed into a bent shape as illustrated in, for example, FIG. 2. Namely, the reference position indicating portion 111 and the size indicating portion 112 are connected to each other by a vertical side portion 121 and a horizontal side portion 122. Since the mask size gauge 100 is formed into the above-described shape, the mask size gauge 100 can be made more difficult to contact with the cheek of the wearer, and the size indicating portion 112 can be made easy to approach the mouth or the like.

Embodiment 3

Figure 3:
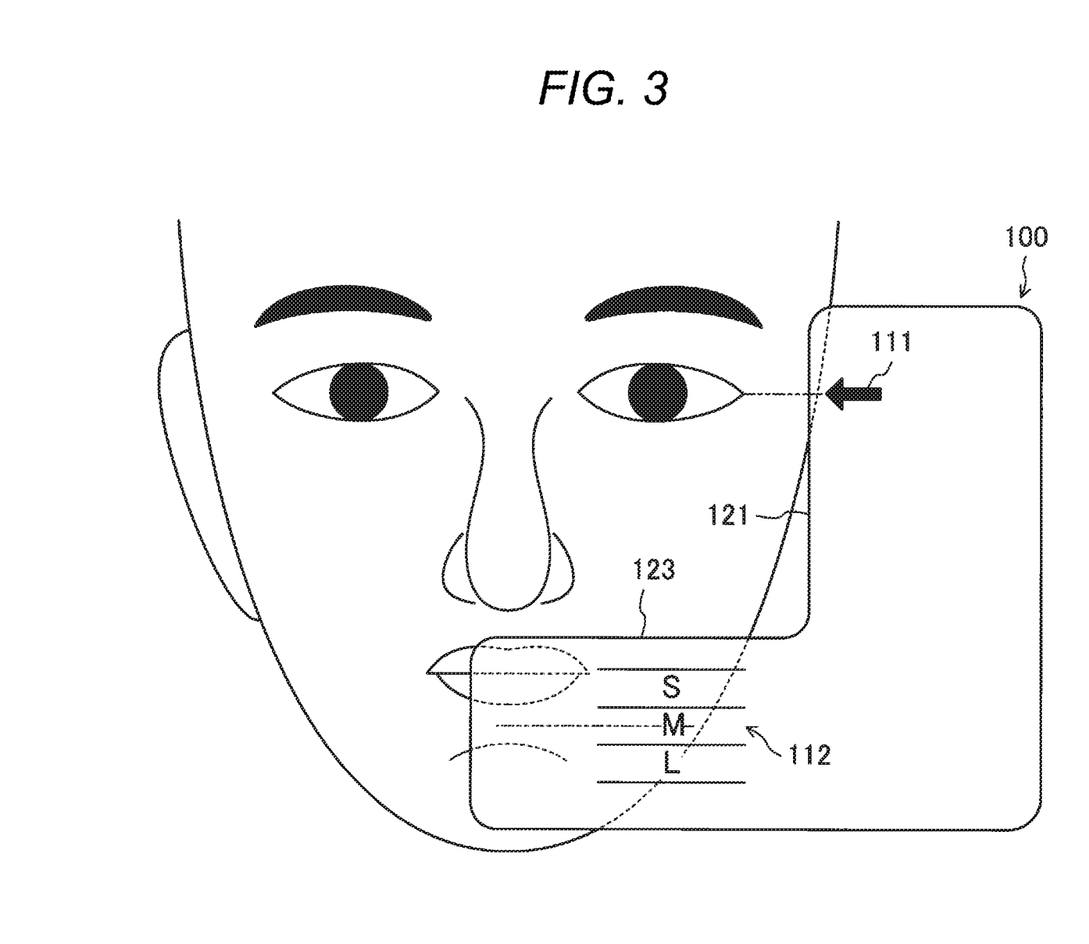
FIG. 3 is a front view illustrating an example of a mask size gauge of Embodiment 3.

In the mask size gauge 100 of Embodiment 3, as illustrated in, for example, FIG. 3, a horizontal side portion 123 that is longer than the horizontal side portion 122 in Embodiment 2 is formed. Even when the horizontal side portion 123 is formed to be somewhat long as described above, a situation where a feeling of discomfort is caused as in the case where the eye of the wearer is covered occurs less frequently. On the other hand, the size indicating portion 112 can be more easily placed closer to the mentolabial sulcus or the like, and therefore the size can be easily selected more correctly.

Embodiment 4

Figure 4:
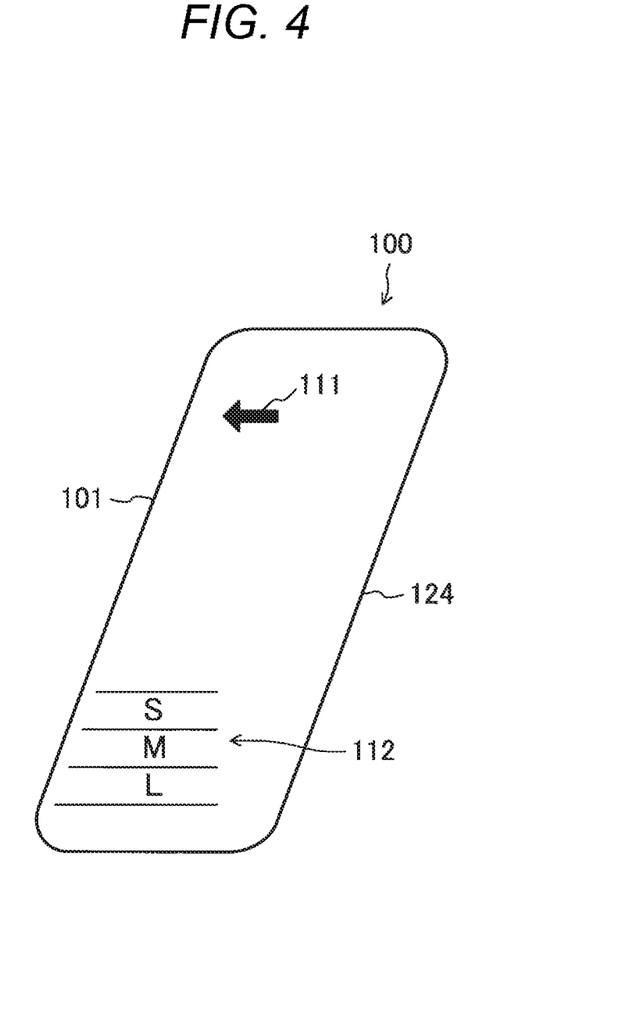
FIG. 4 is a front view illustrating an example of a mask size gauge of Embodiment 4.

In the mask size gauge 100 of Embodiment 4, as illustrated in, for example, FIG. 4, an outer oblique side portion 124 that is parallel to the oblique side portion 101 is formed as a side that is opposed to the oblique side portion 101. Also in the case where the outer oblique side portion is formed in this way, in the same or similar manner as the above-described embodiments, the size of a mask can be selected while placing the mask size gauge 100 on the lateral side of the face of the wearer. Therefore, it is possible to easily avoid a situation where the face or eyes of the wearer are covered by the mask size gauge 100, and a feeling of discomfort is caused, and furthermore the size and weight of the mask size gauge 100 can be reduced.

Embodiment 5

Although, in the above-described embodiments, the example in which the height position of the upper reference part in the upper portion of the face is set as the reference, and the size of a mask is selected in accordance with the height position of the lower reference part in the lower portion of the face has been described, the manner of selecting the size is not limited to this. Conversely, the height position of the lower reference part in the lower portion of the face is set as the reference, and the size of a mask may be selected in accordance with the height position of the upper reference part in the upper portion of the face.

Figure 5:
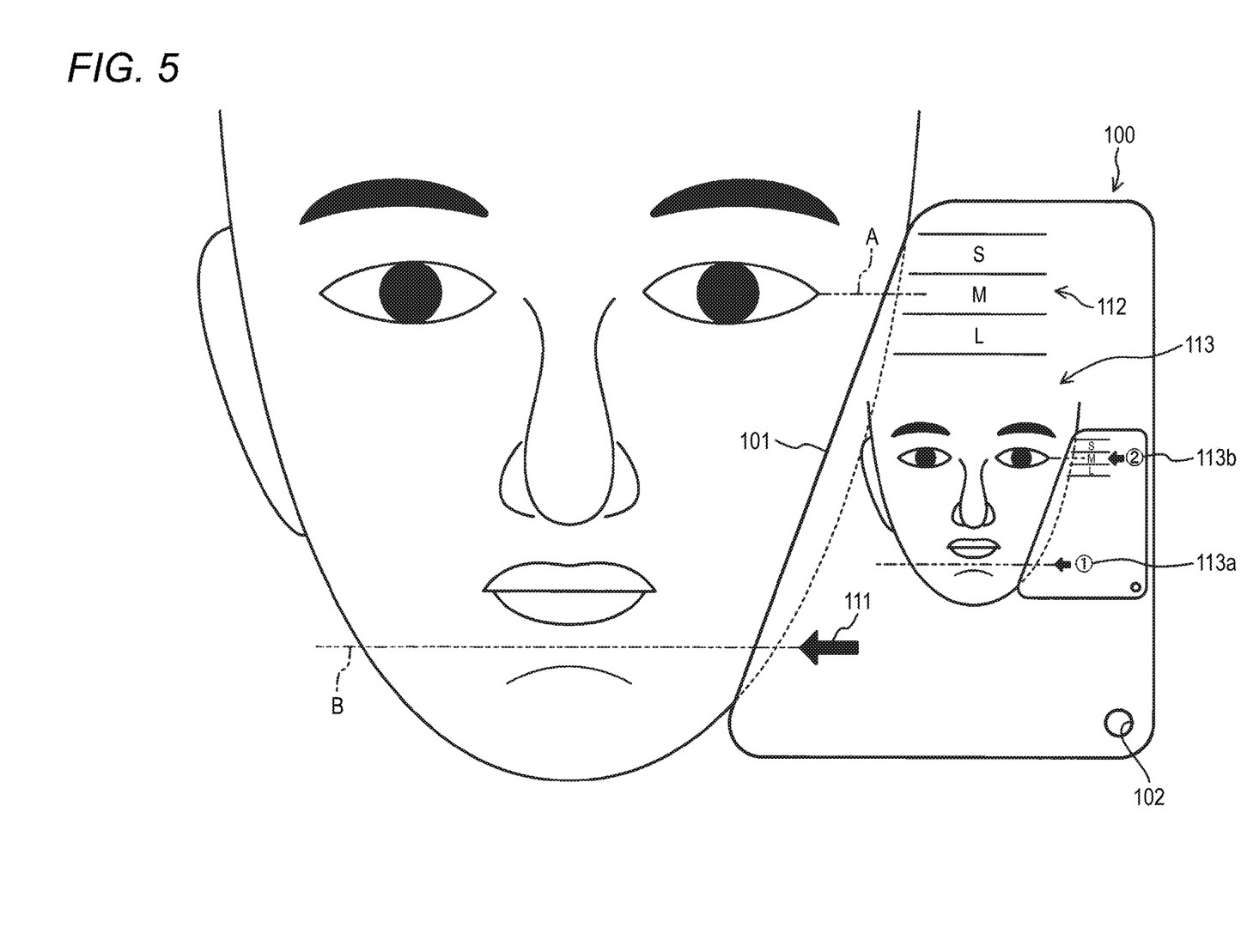
FIG. 5 is a front view illustrating an example of a mask size gauge of Embodiment 5.

Specifically, as illustrated in FIG. 5, for example, the reference position indicating portion 111 in which an arrow shape or the like is printed may be disposed in the vicinity of the lower portion of the oblique side portion 101, and the size indicating portion 112 where, for example, four horizontal index lines and letters S, M, and L are printed may be disposed in the vicinity of the upper portion of the oblique side portion 101. In the example of the figure, the sequence indications 113a, 113b corresponding to the above-described placement are displayed also in the instruction indicating portion 113.

Also in this case, in the same or similar manner, it is possible to attain the effects such as that the size of a mask can be selected while placing the mask size gauge 100 on the lateral side of the face of the wearer.

According to an aspect of the presently disclosed subject matter, there is provided a mask size gauge for selecting a size of a mask in accordance with a distance in a height direction between an upper reference part in an upper portion of a face of a wearer, and a lower reference part in a lower portion of the face of the wearer, the mask size gauge comprising:

a reference position indicating portion indicating that the reference position indicating portion is to be placed at a height position of the upper reference part on an outer lateral side of an eye of the wearer; and a size indicating portion that is located at a position which is closer to a middle of the face than the reference position indicating portion, and that indicates the size of the mask according to a height position of the lower reference part; or the mask size gauge comprising:

a reference position indicating portion indicating that the reference position indicating portion is to be placed closer to a middle of the face than an outermost portion of an eye of the wearer, and at a height position of the lower reference part; and a size indicating portion that indicates the size of the mask according to a height position of the upper reference part in an outer lateral side of the eye of the wearer.

According to the configuration, the size of a mask can be selected while placing the mask size gauge on the lateral side of the face of the wearer. Therefore, a mask of an adequate size can be easily selected while avoiding a situation where the face or eye of the wearer is covered by the mask size gauge, and a feeling of discomfort is caused.

According to the presently disclosed subject matter, a mask of an adequate size can be easily selected without causing a feeling of discomfort in a wearer.

What is claimed is:

1. A mask size gauge for selecting a size of a mask in accordance with a distance in a height direction between an upper reference part in an upper portion of a face of a wearer, and a lower reference part in a lower portion, the mask size gauge comprising:
   a reference position indicating portion indicating that the reference position indicating portion is to be placed at a height position of the upper reference part on an outer lateral side of an eye of the wearer, wherein no portion of the reference position indicating portion extends across the eye; and
   a size indicating portion that is located at a position which is closer to a middle of the face than the reference position indicating portion, and that indicates the size of the mask according to a height position of the lower reference part.

2. The mask size gauge according to claim 1, wherein the upper reference part is one of an eye inner corner, eye outer corner, center of a pupil in a front view, and eyebrow of the wearer.

3. The mask size gauge according to claim 1, wherein the lower reference part is one of a mentolabial sulcus, lower end of a chin, front end of the chin, superior lip, inferior lip, boundary between the superior and inferior lips, and phitrum of the wearer.

4. The mask size gauge according to claim 1, wherein an oblique side portion that, in a posture during use of the mask size gauge, connects the reference position indicating portion and the size indicating portion is formed.

5. The mask size gauge according to claim 4, wherein the mask size gauge has a trapezoidal shape having a vertical side portion that is opposed to the oblique side portion, and horizontal side portions that are formed in upper and lower edges, respectively.

6. The mask size gauge according to claim 4, wherein an outer oblique side portion that is parallel to the oblique side portion is formed as a side that is opposed to the oblique side portion.

7. The mask size gauge according to claim 1, wherein a vertical side portion and a horizontal side portion are formed, the vertical side portion, in a posture during use of the mask size gauge, extending toward a lower side from the reference position indicating portion corresponding to the upper reference part, the horizontal side portion extending from a lower end of the vertical side portion toward an upper position of the size indicating portion corresponding to the lower reference part.

8. The mask size gauge according to claim 1, wherein an instruction indicating portion that indicates a manner of use of the mask size gauge is disposed between the reference position indicating portion and the size indicating portion.

9. The mask size gauge according to claim 8, wherein the instruction indicating portion includes a sequence indication of a procedure indicating that the reference position indicating portion is placed at the height position of the upper reference part of the wearer, and thereafter the size of the mask that is indicated by the size indicating portion according to the height position of the lower reference part of the wearer is read.

10. A mask size gauge for selecting a size of a mask in accordance with a distance in a height direction between an upper reference part in an upper portion of a face of a wearer, and a lower reference part in a lower portion, the mask size gauge comprising:

a size indicating portion that indicates the size of the mask according to a height position of the upper reference part in an outer lateral side of an eye of the wearer; and a reference position indicating portion indicating that the reference position indicating portion is to be placed at a position which is closer to a middle of the face than the size indicating portion, and at a height position of the lower reference part, wherein no portion of the reference position indicating portion extends across the eye.

11. The mask size gauge according to claim 10, wherein the upper reference part is one of an eye inner corner, eye outer corner, center of a pupil in a front view, and eyebrow of the wearer.

12. The mask size gauge according to claim 10, wherein the lower reference part is one of a mentolabial sulcus, lower end of a chin, front end of the chin, superior lip, inferior lip, boundary between the superior and inferior lips, and phitrum of the wearer.

13. The mask size gauge according to claim 10, wherein an oblique side portion that, in a posture during use of the mask size gauge, connects the reference position indicating portion and the size indicating portion is formed.

14. The mask size gauge according to claim 13, wherein the mask size gauge has a trapezoidal shape having a vertical side portion that is opposed to the oblique side portion, and horizontal side portions that are formed in upper and lower edges, respectively.

15. The mask size gauge according to claim 13, wherein an outer oblique side portion that is parallel to the oblique side portion is formed as a side that is opposed to the oblique side portion.

16. The mask size gauge according to claim 10, wherein a vertical side portion and a horizontal side portion are formed, the vertical side portion, in a posture during use of the mask size gauge, extending toward a lower side from the size indicating portion corresponding to the upper reference part, the horizontal side portion extending from a lower end of the vertical side portion toward an upper position of the reference position indicating portion corresponding to the lower reference part.

17. The mask size gauge according to claim 10, wherein an instruction indicating portion that indicates a manner of use of the mask size gauge is disposed between the reference position indicating portion and the size indicating portion.

18. The mask size gauge according to claim 17, wherein the instruction indicating portion includes a sequence indication of a procedure indicating that the reference position indicating portion is placed at the height position of the lower reference part of the wearer, and thereafter the size of the mask that is indicated by the size indicating portion according to the height position of the upper reference part of the wearer is read.

* * * * *